United States Patent
Regni, Jr.

(10) Patent No.: US 6,200,324 B1
(45) Date of Patent: Mar. 13, 2001

(54) METHOD AND APPARATUS FOR SHAPING A SITE FOR ANCHORING AN IMPLANT AND TO PROVIDE BONE AUGEMENTATION AND SHAPE CONFORMITY

(76) Inventor: Gerald J. Regni, Jr., 937 Christian St., Philadelphia, PA (US) 19147

( * ) Notice: Subject to any disclaimer, the term of this patent is extended or adjusted under 35 U.S.C. 154(b) by 0 days.

(21) Appl. No.: 09/388,402

(22) Filed: Sep. 1, 1999

(51) Int. Cl.⁷ .................................................. A61B 17/66
(52) U.S. Cl. ........................... 606/105; 606/57; 606/60; 606/78; 433/173
(58) Field of Search .............................. 606/105, 57, 60, 606/78, 70, 68, 69, 62, 63, 64, 58, 59, 170, 80; 433/165, 166, 173; 623/22.18, 22.37

(56) References Cited

U.S. PATENT DOCUMENTS

| | | | |
|---|---|---|---|
| 4,787,848 | * 11/1988 | Ross ...................................... | 433/165 |
| 5,051,091 | * 9/1991 | Rosenfeld ............................ | 433/173 |
| 5,310,408 | * 5/1994 | Schryver et al. ................... | 623/22.37 |
| 5,686,116 | 11/1997 | Bockman et al. ................... | 424/650 |
| 5,704,938 | * 1/1998 | Staehlin et al. ...................... | 606/105 |
| 5,797,741 | 8/1998 | Bonpard et al. ...................... | 433/75 |
| 6,033,412 | * 3/2000 | Losken et al. ....................... | 606/105 |

* cited by examiner

Primary Examiner—Pedro Philogene
(74) Attorney, Agent, or Firm—Volpe and Koenig. P.C.

(57) ABSTRACT

Method and apparatus for providing a socket of uniform shape within a bone preparatory to receipt of an anchoring member of an implant or augmentable bone. The tool is placed in a cavity in which a diseased bone or bone portion has been removed. A substantially cylindrical-shaped tool is inserted within the cavity. Grip extenders are selectively projected from the tool to secure the tool in place preparatory to its operation. The side walls and tip are expanded, preferably in a reciprocating fashion, compressing adjacent walls of the cavity modifying their length and width and making the sidewalls more uniform to assure precision placement of an augmented bone while providing a more uniform cavity shape and a more enriched site for a transplant, implant and/or bone augmentation. The resulting socket is scanned and a the scan is employed to prepare the augmented bone whereupon the implant may then be interfaced with the augmented bone in a highly precise manner.

15 Claims, 8 Drawing Sheets

Step 3
Surefit placed into defective extraction site.

Step 2
Extraction site creating abnormal defect.

Step 1
Diseased periodontal support system.

Step 6
Implant interfaced with augmented bone.

Step 5
Socket scanned to prepare aigmented bone and create optimum intinacy and retention.

Step 4
Surefit modifying length and width of defect for precision placement of augmented bone.

Step 9
Optimum placement of implant into ideal extraction site.

Step 8
Conservative modification compressing bone to desired length and diameter.

Step 7
Surefit placed into defective extraction site.

METHOD AND APPARATUS FOR SHAPING A SITE FOR ANCHORING AN IMPLANT AND TO PROVIDE BONE AUGEMENTATION AND SHAPE CONFORMITY

FIELD OF THE INVENTION

The present invention relates to method and apparatus for preparing a socket and more particularly to providing a method and apparatus which forms a socket of substantially uniform size and shape preparatory to receiving an implant which may be augmentable bone or a transplant.

BACKGROUND OF THE INVENTION

There are a number of situations requiring implantation of a prosthesis. As one particular example, when it becomes necessary to remove a diseased tooth, it is typically replaced with a prosthesis. For the last fifteen years implantologists have been resigned to adapting to an oral cavity from which the diseased tooth has been removed. The existing situation has led to a non-consistent predictability as to such implantations which result from the following five factors:

1. the competency of the doctor (implantologist or prosthodontist);
2. the availability of bone and the proper configuration thereof;
3. the patient's immunological system and habits that may contribute to accelerated breakdown;
4. the compliance of the patient including the immune system function which will be handled holistically.
5. non-predictable bone augmentation procedures.

The method and apparatus of the present invention serves to assure significantly more consistent predictability by providing a tool, for orthopedic use, which enhances and augments deficient bone in any surgical recipient site and thereby provide ideal standards having uniform predictability which provide implantologists and all prosthodontists using the tool to provide excellent results even in compromised situations having versatile parameters, which create optimum solutions and eliminate mediocrity.

BRIEF DESCRIPTION OF THE INVENTION

The tool of the present invention and its method of use provides a fully integrated, stable, aesthetic biocompatible, structurally functional device which is perfectly adaptable to each individual, is simplified in its operation and which provides significantly enhanced predictable results of augmenting and implanting. The tool is comprised of an elongated cylindrical member having a hemispheric tip. The tip and side walls are expandable by rotating power or air pressure and are controlled for expansion by an air operated pump chamber for introducing air under pressure into the tool or by a lead screw.

The region between the tip and cylindrical, expandable side walls is provided with a plurality of grip extenders which are selectively projectable in an outward radial direction to anchor the tool preparatory to the expansion operation. The tool is placed into the cavity at the extraction site or surgical site and is expanded and contracted in a repeated fashion, compressing the side walls and base of the cavity providing a socket of more uniform dimensions and a site more densely enriched with bone and blood supply and cells to give the best bond and integration. The tool is then deflated and removed from the socket which is then scanned by a scanning device for determining the shape and volume of the socket in order to establish the amount and shape of augmented bone or transplant required for optimum intimacy and retention. The augmented boned is then shaped and placed into the cavity. The anchoring member of the implant is then inserted into the augmented bone.

OBJECTS OF THE INVENTION

It is therefore one object of the present invention to provide a novel method and apparatus for preparing a site within a bone for receipt of transplant synthetic or autogenesis or implant.

Another object of the present invention is to provide a novel tool for preparing a site for an implant having the capability of compressing bone within the cavity of the site to provide a more uniform socket for receipt of an implant which significantly enhances the precision placement of the implant or existing size or a scan and cut of a prosthetic component to fit on site.

BRIEF DESCRIPTION OF THE FIGS.

The above as well as other objects of the present invention will become apparent when reading the accompanying description and drawings in which:

FIGS. 2b–2f show more detailed views of members employed in the separating assembly shown in FIG. 2a.

DETAILED DESCRIPTION OF THE INVENTION AND PREFERRED EMBODIMENTS THEREOF

Figure 1:
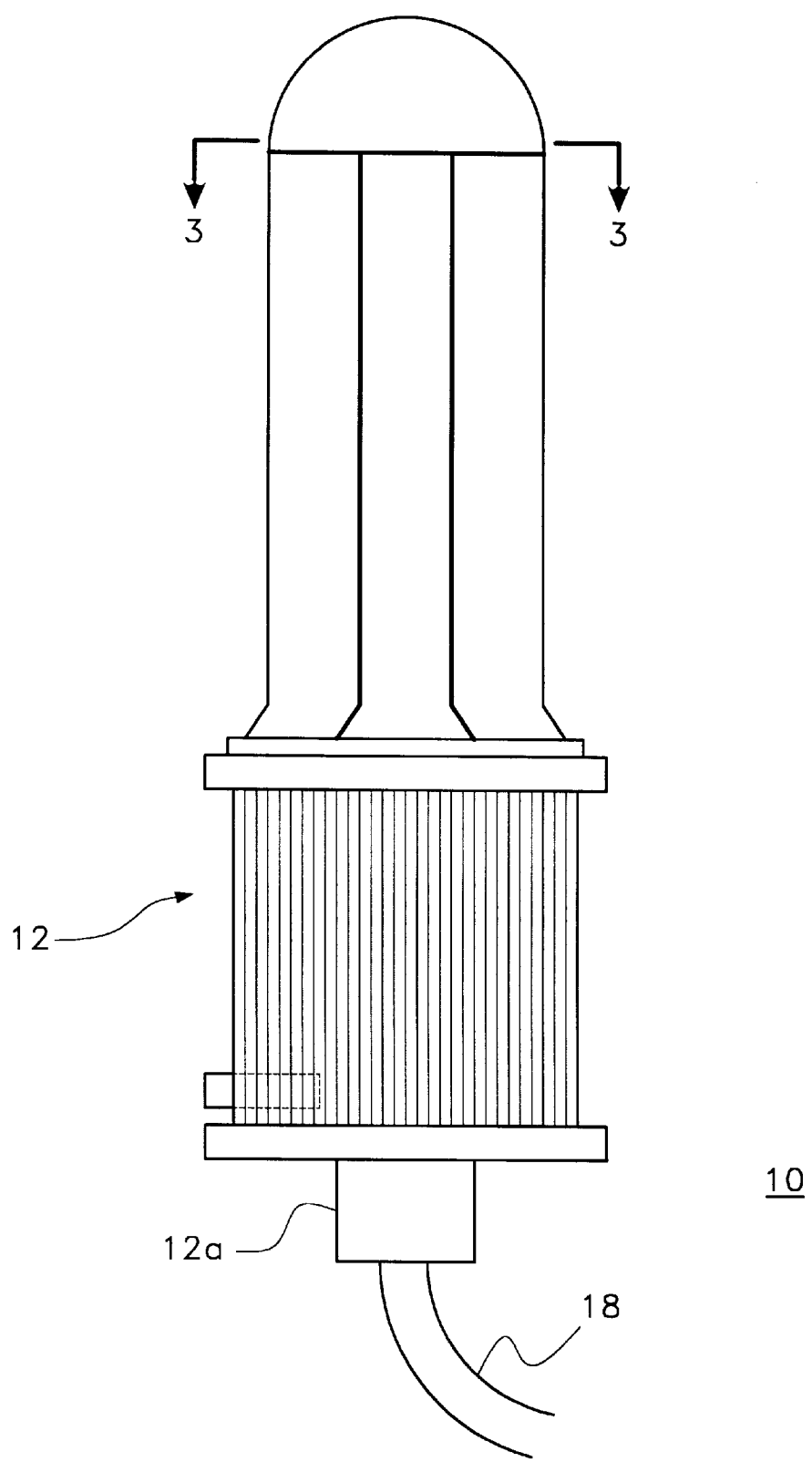
FIG. 1 shows an external side view of the tool embodying the principles of the present invention.
Figure 2A:
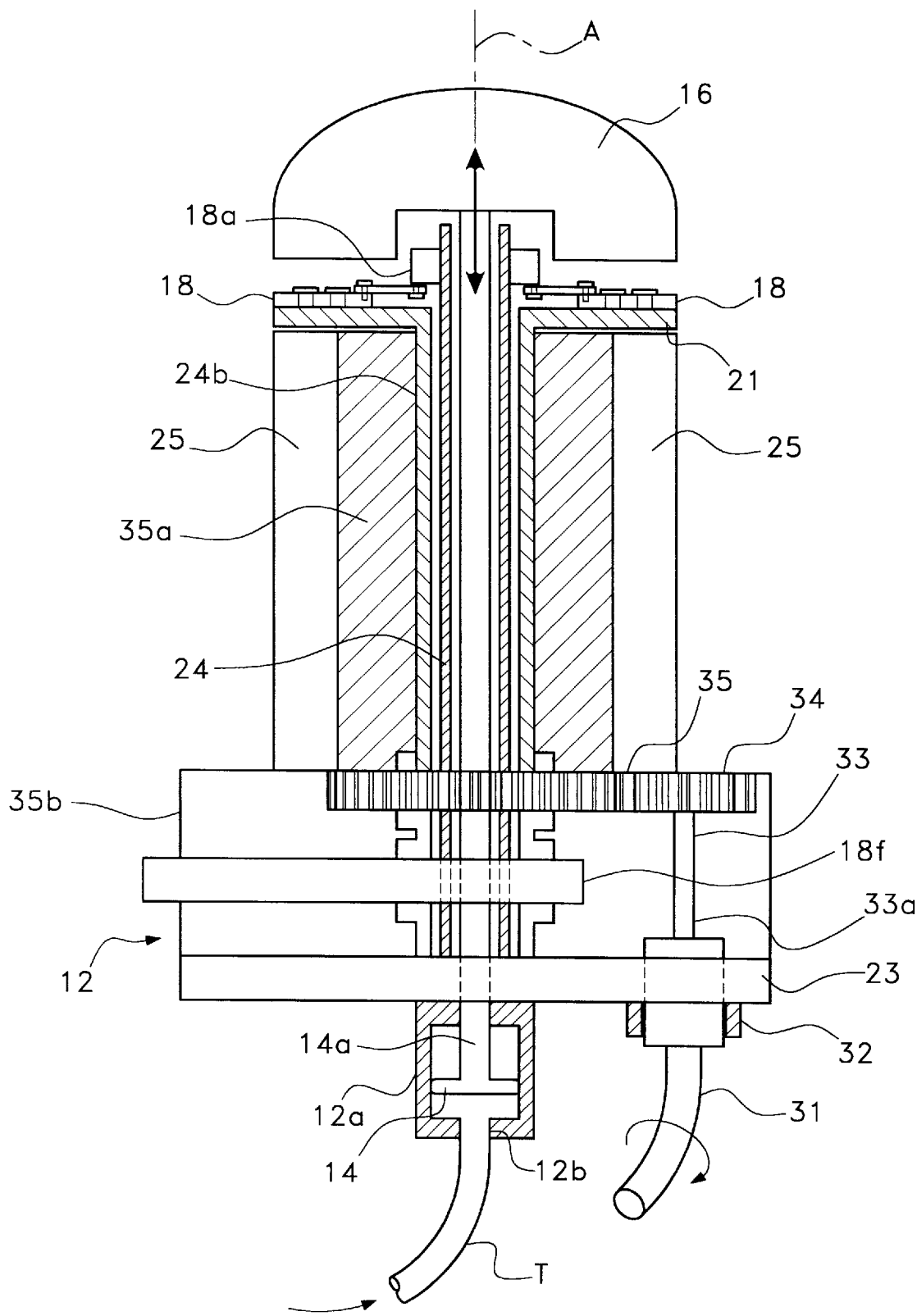
FIG. 2a shows a cross-sectional view of the tool of FIG. 1, looking in the direction of arrows 2a—2a in FIG. 1.
Figure 2B:
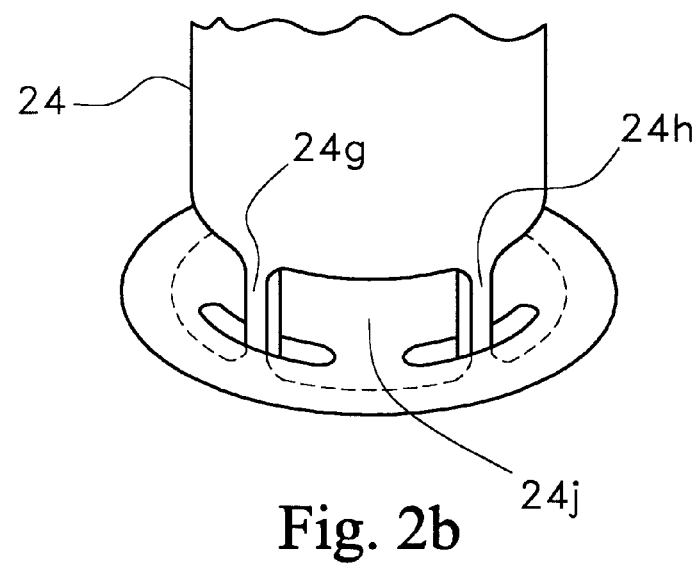
Figure 2C:
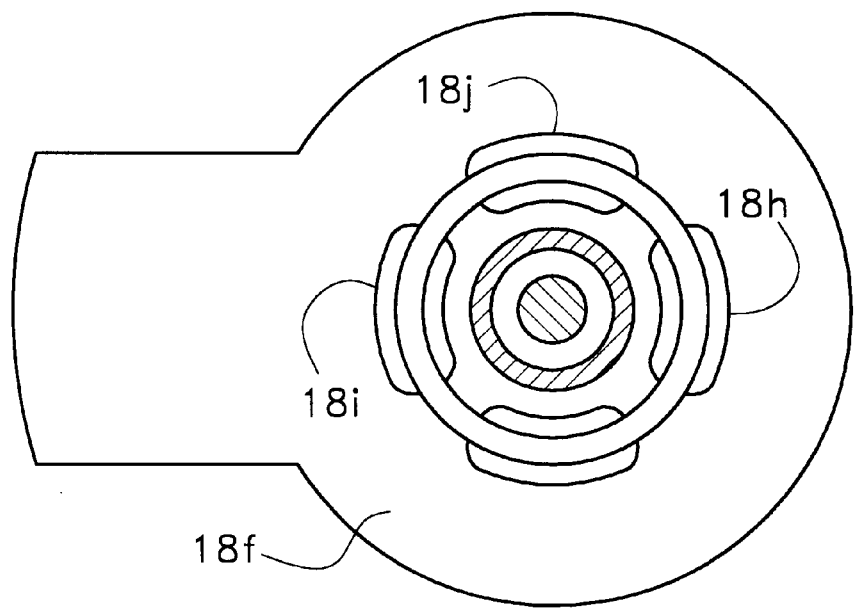
Figure 2D:
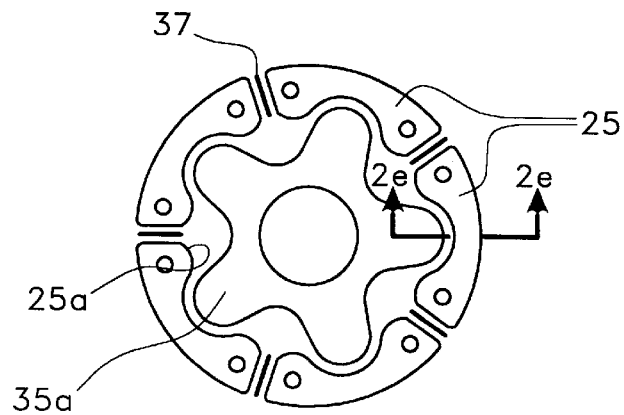
Figure 2E:
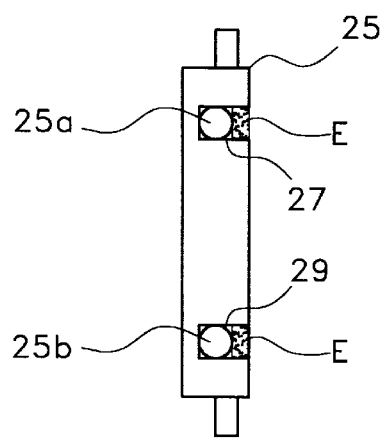
Figure 2F:
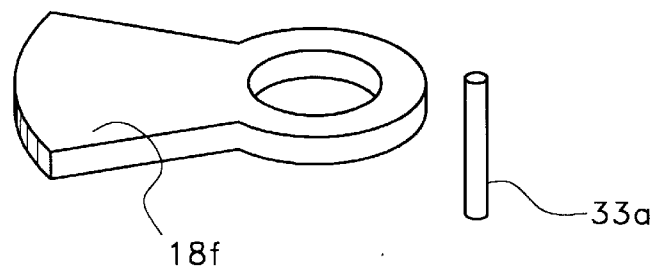
Figure 3:
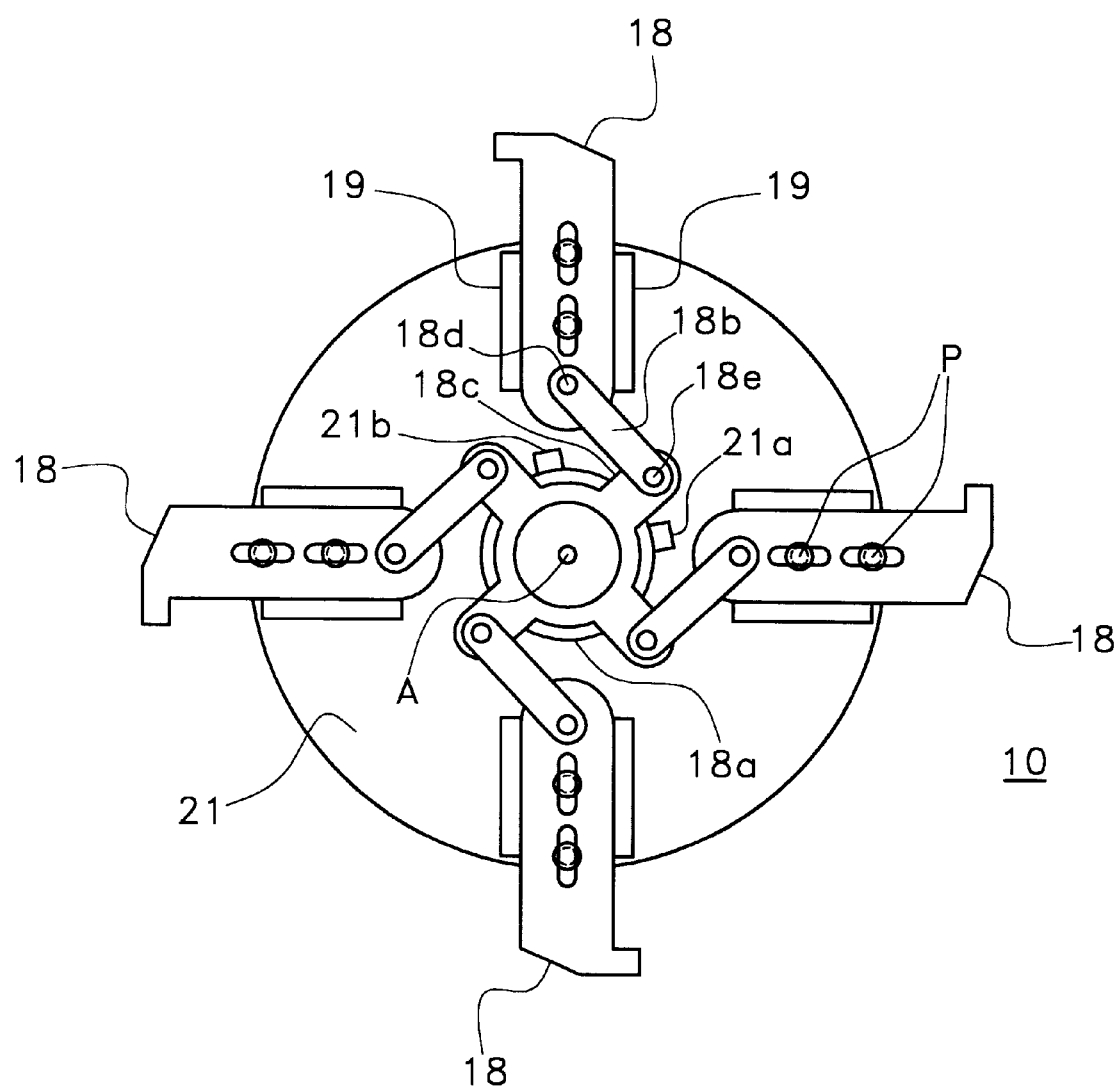
FIG. 3 is a top view of the tool of FIG. 1, looking in the direction of arrows 3—3 in FIG. 1.

Making reference to FIGS. 1–3, there is shown therein a tool 10 designed in accordance with the principles of the present invention and comprised of a base member 12 having a centrally located, cylindrically-shaped pump chamber 12a in which a piston 14 is reciprocally mounted. A piston rod 14a is integrally joined to piston 14 and extends the length of the tool and into tip portion 16. Air under pressure is introduced from a source (not shown) through tubular member T and a bore 12b, causing piston rod 14, which extends upwardly and into the tip 16, to be lifted upon the introduction of air pressure into the lower end of chamber 12a, in the manner shown in FIG. 4d. Four (4) grip extenders 18 (see FIG. 3), provided at 90 degree intervals immediately beneath the tip 16, are extended outwardly under the control of a hollow cylinder 18a, rotatable about its longitudinal axis (see FIGS. 2a and 3). Linkage arms 18b are pivotally mounted to pivot 18e on projections 18c provided on cylinder 18a. Each arm 18c is pivotally mounted at its opposite end to an extender 18 by a pivot pin 18d. The extenders are each either slidably mounted between a pair of guides 19 provided on a fixed upper plate 21 or guided by pins P mounted upon plate 21 and slidable within slots 18g. The upper plate also has a pair of integral stops 21a, 21b provided thereon.

In operation, when cylinder 18a is rotated clockwise, arms 18b pull their extenders 18 inwardly, further movement being stopped by stop 21a. When cylinder 18a is rotated counter-clockwise, each pivot 18e moves over dead-center and movement stops by stop 21b, causing the extenders to move outwardly and "bite" into the cavity near the base thereof (see FIG. 4c) By moving slightly past over-center, the extenders are held in this position.

The cylinder 18a is rotated by means of a manually rotatable lever member 18f located above a lower fixed plate 23. The arcuate outer periphery of member 18f is preferably knurled to facilitate gripping and rotation thereof, whereby extenders 18 become anchored into the side walls of the cavity.

Lower anchor plate 23 is joined to the lower end 24a of a fixed, hollow cylinder 24. The upper end 24b of cylinder 24 is fixedly secured to upper mounting plate 21. Piston rod 14a extends through anchor plate 23, outer cylinder 24, inner cylinder 18a, a central opening in knurled lever member 18f and a central opening in upper mounting plate 21. The upper end of piston rod 14a is joined to dome-shaped tip 16 for reciprocating the tip upon application of air pressure. The piston rod may be spring-loaded to return the dome 16 to the collapsed position or may be reciprocated by alternately applying pressure on opposite sides of the piston 14. Alternatively, the piston chamber may be replaced with an electromagnet, preferably operated by an a.c. source (not shown) operating upon the rod 14a (in a reciprocating manner) coupled to a plunger of the electromagnet. If desired a rotatable lead screw may be employed to selectively raise and lower tip 16.

The sidewalls 25 arranged between lower anchor plate 23 and upper plate 21 are each provided with upper and lower arcuate recesses 25a, 25b (see FIG. 2e). Resilient coil springs 27, 29 are respectively seated in the upper and lower slots 25a, 25b in the sidewalls 25, normally urging the sidewalls inwardly. The open ends of the recesses are sealed with a suitable material, such as an epoxy E, which does not interfere with the expansion and contraction of the springs 27, 29 while providing a substantially smooth outer surface.

A source of rotating power, or orthopedic surgeon's drill as a source for powering a dental drill, is coupled through a flexible, rotatable cable 31 to a coupling 32 arranged to extend from the undersurface of lower plate 23. Coupling 32 is joined to the lower end 33a of a shaft 33 which extends upwardly and clear of the small-diameter portion 18f−1 of the knurled lever member 18f, enabling clockwise and counterclockwise rotation of member 18f through a fixed angle (controlled by stops 21a, 21b) without interfering with the rotation of shaft 33 and vice versa.

The upper end 33b of shaft 33 is joined to a small diameter gear 34 which meshes with a larger diameter gear 35. Gear 35 has a central opening of a diameter sufficient to provide clearance for cylinder 24. Cylinder 24 has a pair of upper and lower bosses 24e, 24f for positioning gear 35 therealong. A similar pair of bosses 24f, 24g retain the knurled lever member at a fixed position along cylinder 24. The knurled lever member 18f and gear 35 are preferably provided mounted upon cylinder 24 by suitable bearings arranged between the cylinder 24 and each of the members 18f, 35.

An annular member 35a has its lower end 35b integrally joined to the upper surface of gear 35. The outer periphery has a corrugated or fluted surface contour comprised of alternatively convex and concave shaped surfaces, which engage a similar shaped surface provided on each of the interior surfaces 25a of each of the sidewall sections 25. As the gear 35 is rotated (driven by members 31, 32, 33 and 34), the sidewall sections are reciprocated outwardly and inwardly thereby impacting upon the sidewalls of the cavity into which tool 10 is inserted, to thereby enlarge the cavity and make its sidewalls more uniform as to conform to the shapes of the reciprocating sidewalls (see FIGS. 4a–4c). Roller bearings may be provided between the engaging surfaces of the members 35a and 25.

A plurality of radially aligned guide plates 37 (see FIGS. 2a and 2d) have their upper and lower ends respectively secured to the underside of plate 21 and the upper surface of a plate 38 forming a cage-like structure. Each adjacent pair of guides limits the movement of elements 25 to inward and outward movement in the radial direction. The elements 25 may each be provided with a pair of guide pins 25c respectively at the upper and lower surfaces thereof, which are guided within cooperating radially aligned slots (or grooves) 21d and 38a respectively provided in plates 21 and 38.

The knurled lever member 18f is further provided with a plurality of arcuate-shaped openings, 18h, 18i 18j and 18k (see FIGS. 2b and 2c). Cylinder 24 is provided with cooperating cutaway portions, such as 24i, 24j, 24k, 24l (see FIG. 2b), leaving strut-like portions, such as 24g, 24h. The strut-like portions each extend through an associated one of the arcuate cut-outs 18h, 18i, 18j, 18k, enabling the member 18f to be selectively rotated without interfering with the cylinder 24, for selectively moving extenders 18 in and out under control of member 28 and cylinder 18a.

FIG. 1, showing a side view of tool 10, shows typical dimensional relationships for tool 10 when utilized for performing dental implants, it being understood that the present invention may be utilized for other bone implants or other bone augmentation in other parts of the body.

Figure 4C:
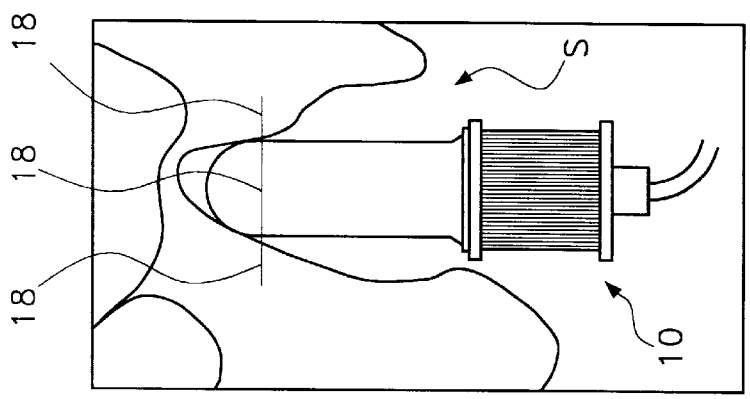
FIGS. 4a–4f show the procedural steps employing the novel tool of the present invention.
Figure 4B:
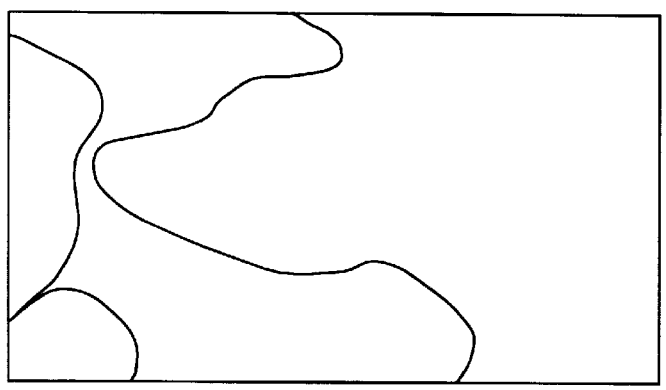
Figure 4A:
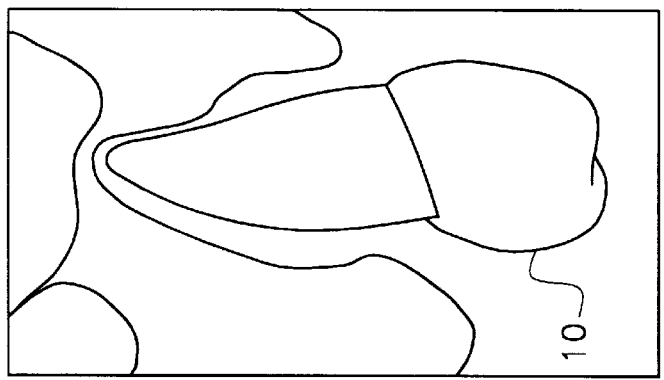

FIGS. 4a–4f show various stages of the implant procedure. FIG. 4a show a diseased periodontal support system requiring corrective action. The tooth T, shown in FIG. 4a, is extracted, leaving an extraction site creating an abnormal defect, as shown in FIG. 4b. It can be seen that the cavity resulting from the extraction has an irregular shape, making it extremely difficult to provide proper and precise alignment for a prosthesis.

In FIG. 4c, tool 10 is placed into the defective extraction site. The grip members 18 are extended, anchoring the tool within the cavity and near the base thereof. The tip portion 16 is urged upwardly and the sidewalls 25 are urged outwardly to modify all dimensions of the defective extraction site (i.e. length, width, depth, etc.) to facilitate precision placement of augmented bone or implant. FIG. 4d shows the manner in which tip 16 and sidewalls 25 are expanded. The result of this expansion causes the engaging side walls of the cavity to compress, resulting in a significantly more uniform socket, as shown in FIG. 4e. A comparison of the resulting socket, show in FIG. 4e, with the original defective area, shown in FIG. 4c, clearly indicates the enhanced uniformity of shape of the socket S. The tool 10 is preferably turned off and rotated about its longitudinal axis one or more times to assure that the walls of the cavity are uniformly compressed.

The socket may then be scanned by any suitable scanning device, such as the CEREC 1.11 and CEREC 2, manufactured by Sirona Dental Systems of Bensheim, Germany, or an other device having similar capabilities, in order to prepare augmented bone or implant and create optimum intimacy and retention. The compression of the side walls further enhances their strength and receptiveness to augmented bone and the intimate adhesion therewith, by creating a dense, enriched bed site.

The amount of augmented bone determined by the scanning operation is then introduced into the cavity.

Figure 4F:
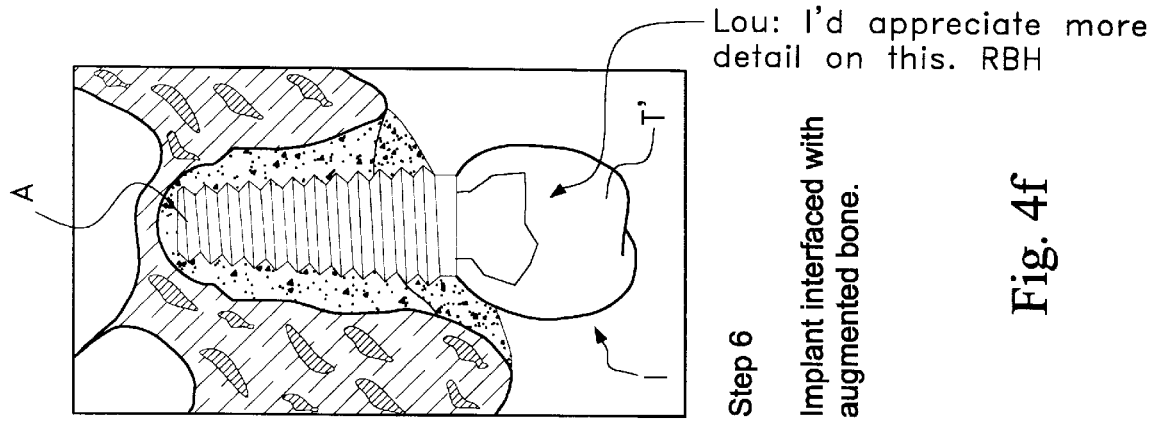
Figure 4E:
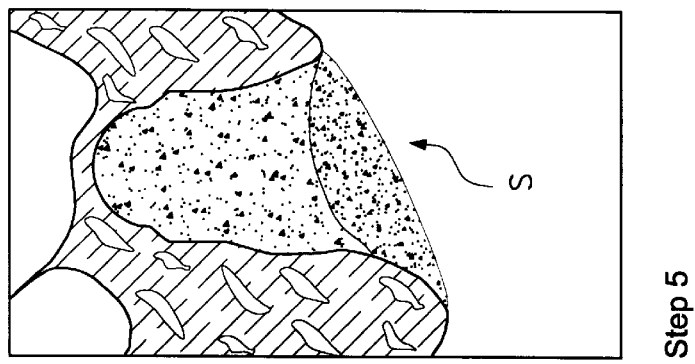
Figure 4D:
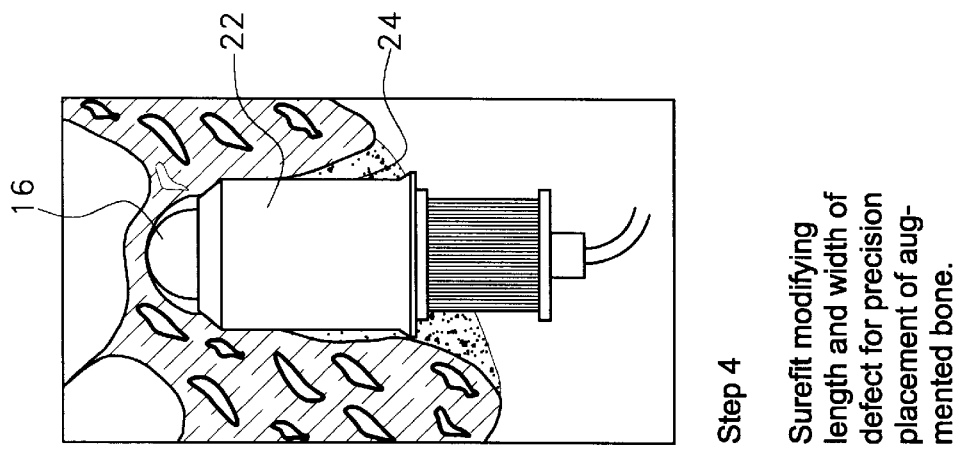

Thereafter, as shown in FIG. 4f, the implant I comprised of a prosthetic tooth T' and an anchoring portion A, is placed into the augmented bone. A hole is drilled in the augmented bone after its insertion and the implant is either threaded or tapped into the opening. The shape of socket S, shown in FIG. 4e and 4f, facilitates the capability of precision placement and alignment of the prosthesis T' within the socket and relative to adjacent teeth, for example, alignment of the drilling or pre-drilled or pre-made hole in the bone.

Figure 5C:
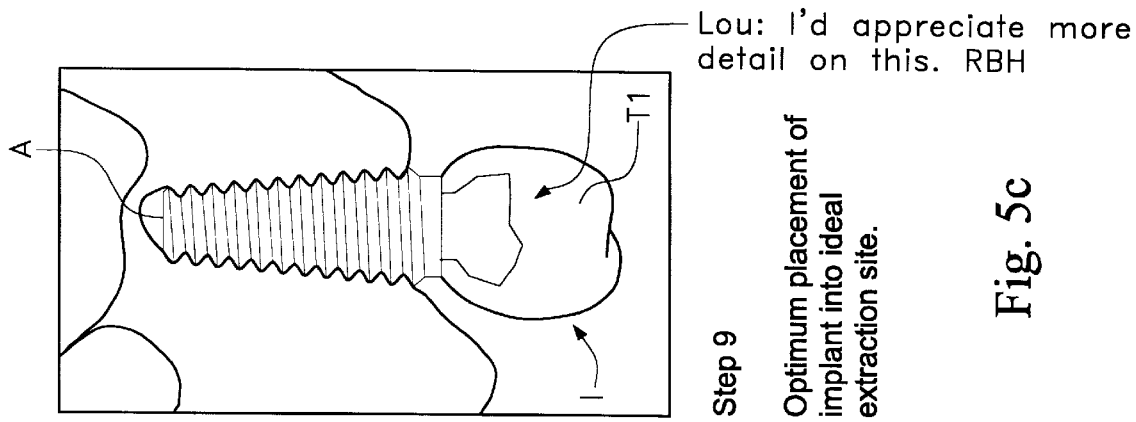
FIGS. 5a–5c show the procedural steps for a more conservative modification.
Figure 5B:
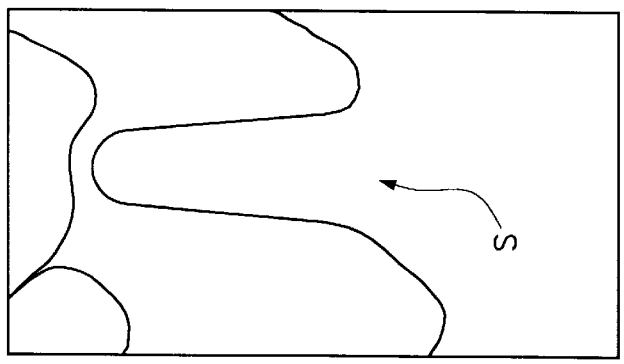
Figure 5A:
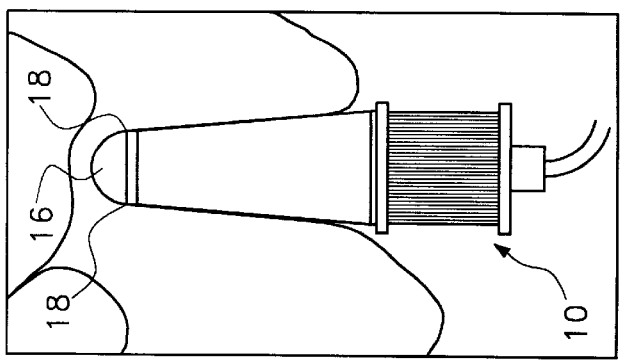

FIGS. 5a–5c show the process of the present invention in a case where the extract site requires less severe modification.

After extraction of the tooth, tool 10 is placed into the defective extraction site, the tool is operated to lift tip portion 16 and embed the grip extenders into the adjacent bone near the base of the cavity resulting from the extraction. The expansion cylinders 22 and 24 are expanded by the introduction of air under pressure, as shown in FIG. 5a, compressing the surrounding walls. The tool is then removed, leaving a socket S, as shown in FIG. 5b, in which the bone engaged by tool 10 is compressed to a desired length and diameter. Comparing FIG. 5b with FIG. 4e, can be seen at the modification in FIG. 5b is much more conservative in nature.

The implant I having an anchoring portion A and a prosthesis portion T' can be seen to closely match the size and shape of the extraction site as a result of the compression of the surrounding bone by the novel tool of the present invention.

Although FIG. 1 shows typical dimensions in applications for a tooth implant, it should be understood that the dimensions of the tool may be altered to be smaller or larger than those shown in FIG. 1, depending upon the particular application. In addition, it should be noted that the present invention is not limited to applications for performing tooth implants, but may be utilized for other oral, as well as non-oral implants, such as orthapedic prosthesis or surgical procedures, requiring precise dimensional modifications, and augmentation, for example.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention described herein.

What is claimed is:

1. A method preparing a cavity in a bone comprising the steps of:
   (a) placing a tool having expandable, annular-shaped side walls within said cavity so that a hemispheric end of said tool is adjacent to the base of said cavity;
   (b) expanding the side-walls of said tool sufficient to compress adjacent side walls of said cavity and extending the moveable tip of the side walls to more intimately engage the base region of the cavity thereby compressing the adjacent side walls of the cavity to form a more uniform shaped socket for receipt of an implant.

2. The method of claim 1 further comprising extending grip expanders adjacent to the tip of the tool into the side wall portions of the cavity to anchor the tool in place within the cavity during the bone compression operation.

3. The method of claim 1 further comprising:
   (c) removing the tool from the cavity;
   (d) determining the shape and volume of the socket formed by the compression operation to determine the amount of augmented bone needed to fill the cavity with desirable enhancements; and
   (e) placing the amount of augmented bone determined in step (d) in the socket resulting from the compression operation of step (b).

4. The method of claim 3 further comprising:
   (f) providing an implant comprised of a prosthesis and an anchor member integrally joined thereto and inserting the anchor member into the augmented bone.

5. Apparatus for compressing adjacent side walls of a cavity into which a tool is inserted, said tool comprising:
   a base member having a hollow air chamber for receiving air under pressure from a suitable pressurized air source;
   an expandable annular sidewall assembly comprised of a plurality of movable elements mounted upon said base, and rotatable means for moving said elements inwardly and outwardly to compress cavity walls engaged by said elements;
   a reciprocally mounted hemispheric-shaped tip arranged at a free end of a hollow cylinder opposite said base member and means for selectively extending said tip outwardly and away from said cylinder responsive to the introduction of air under pressure into said chamber.

6. The apparatus of claim 5 further comprising a plurality of grip extenders arranged in the region between said hemispheric tip and the adjacent end of said expandable cylinder and means for extending said grip extenders so as to grip portions of the cavity adjacent to the grip extenders and means for extending the grip extenders radially outwardly to hold the tool in place in the cavity during the time that the movable elements are moved outwardly.

7. The apparatus of claim 5 further comprising a piston arranged in said chamber;
   a piston rod coupled between said piston and said tip portion for extending said tip portion upon the introduction of air under pressure into said chamber.

8. The apparatus of claim 5, said means for extending further comprising a manually movable member for selectively moving said extenders inwardly and outwardly.

9. The apparatus of claim 5 wherein said rotatable means comprises a gear rotatably mounted upon said cylinder and including an integral member for expanding and collapsing said element.

10. The apparatus of claim 9 further comprising drive means for rotating said gear and having a driven coupling for receiving a rotatable drive element.

11. The apparatus of claim 10 wherein said drive element is a flexible rotatable member having one end releasably joined to said coupling driven coupling and another end driven by a rotating drive source.

12. The apparatus of claim 11 wherein said integral member has an arcuate-shaped opening, a portion of said drive means extending therethrough for enabling said drive means and said integral member to operate without interference.

13. The apparatus of claim 8 wherein said manually movable member is rotatably mounted upon said cylinder.

14. The apparatus of claim 9 wherein said elements are retained by resilient members which yield when said elements are driven outwardly.

15. The apparatus of claim 5 wherein said cylinder is joined at its lower end to said base member;
   a support plate mounted to another end of said cylinder; and
   said means for extending including a second cylinder extending through said first-mentioned cylinder.

* * * * *